(12) United States Patent
Wang et al.

(10) Patent No.: US 11,851,401 B2
(45) Date of Patent: Dec. 26, 2023

(54) METHOD OF PREPARING UNSATURATED HYDROCARBONS BY BLACK BODY PHOTOCATALYTIC CONVERSION OF SATURATED HYDROCARBON

(71) Applicants: THE CHINESE UNIVERSITY OF HONG KONG, SHENZHEN, Guangdong (CN); University of Toronto, Toronto (CA)

(72) Inventors: Lu Wang, Guangdong (CN); Geoffrey Alan Ozin, Toronto (CA); Zeshu Zhang, Guangdong (CN); Xue Ding, Guangdong (CN); Zhigang Zou, Guangdong (CN)

(73) Assignees: THE CHINESE UNIVERSITY OF HONG KONG, SHENZHEN, Guangdong (CN); UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 17/964,106

(22) Filed: Oct. 12, 2022

(65) Prior Publication Data
US 2023/0202949 A1    Jun. 29, 2023

(30) Foreign Application Priority Data
Dec. 27, 2021    (CN) .......................... 202111615641.4

(51) Int. Cl.
C07C 5/32    (2006.01)

(52) U.S. Cl.
CPC .......... *C07C 5/324* (2013.01); *C07C 2523/06* (2013.01)

(58) Field of Classification Search
CPC ........................... C07C 5/324; C07C 2523/06
See application file for complete search history.

(56) References Cited

FOREIGN PATENT DOCUMENTS

WO    WO-2016096287 A1 *  6/2016 ............. B01D 3/009

OTHER PUBLICATIONS

The translation of WO-2016096287 A1.*

* cited by examiner

*Primary Examiner* — Thuan D Dang
(74) *Attorney, Agent, or Firm* — IP & T GROUP LLP

(57) ABSTRACT

The present disclosure provides a method of preparing unsaturated hydrocarbons by black body photocatalytic (thermal radiative catalytic) conversion of saturated hydrocarbons. In this method, a saturated hydrocarbon reaction gas is introduced into a reaction furnace, and the saturated hydrocarbon is catalyzed to convert under heating and illumination conditions to prepare the unsaturated hydrocarbons. The photocatalysis is combined to the conventional thermal catalysis to improve the catalytic performance, accelerate the reaction speed, increase the conversion rate, and/or improve the selectivity of the catalytic reaction.

12 Claims, 3 Drawing Sheets

METHOD OF PREPARING UNSATURATED HYDROCARBONS BY BLACK BODY PHOTOCATALYTIC CONVERSION OF SATURATED HYDROCARBON

CROSS-REFERENCE TO RELATED APPLICATION

The present disclosure claims the priority to the Chinese patent application with the filing No. 202111615641.4 filed on Dec. 27, 2021 with the Chinese Patent Office, and entitled "Method of Preparing Unsaturated Hydrocarbon by Thermal Radiative Catalyzing of Conversion of Saturated Hydrocarbon", the contents of which are incorporated herein by reference in entirety.

TECHNICAL FIELD

The present disclosure relates to the technical field of chemical industry, and in particular to a method of preparing an unsaturated hydrocarbon by blackbody photocatalytic (thermal radiative) catalyzing of the conversion of saturated hydrocarbon.

BACKGROUND ART

Fossil powered heterogeneous catalysis is the backbone of the chemical and petrochemical industries, responsible for producing hundreds of millions of tons of commodity chemicals and fuels. Associated with these large-scale industrial processes is a massive carbon footprint, a major contributor to climate change.

Saturated hydrocarbons relate mostly to alkanes, while unsaturated hydrocarbons refer primarily to olefins, alkynes, aromatics, etc. Low-carbon olefins relate primarily to ethylene, propylene, and butylene, which are all major organic chemical raw materials and play a significant role in the national economy. The largest consumption of ethylene is in the production of polyethylene, accounting for about 45% of the consumption of ethylene; and ethylene is also used in the production of dichloroethane, vinyl chloride, ethylene oxide, ethylene glycol, styrene, and so on. The majority of propylene is used in the synthesis of polypropylene, as well as acrylonitrile, isopropanol, phenol, acetone, butanol, octanol, acrylic acid, etc. Butylene is used largely for the manufacturing of butadiene, as well as methyl ethyl ketone, sec-butyl alcohol, epoxy butane, and butylene polymers and copolymers. Consequently, the demand for ethylene and propylene is increasing fast, with propylene being in higher demand than ethylene. Although the manufacturing of low-carbon olefins is mostly dependent on fossil fuel, the finding of vast quantities of shale gas and combustible ice increased the yield of low-carbon alkanes and facilitated the dehydrogenation-based synthesis of low-carbon olefins.

The existing ethylene production mainly depends on naphtha steam cracking technology, but the technology has the drawbacks including high reaction temperature (>750° C.), high-energy consumption, low selectivity (about 75%), and short lifetime. The existing propylene is mainly prepared by catalyzing propane to dehydrogenize with a catalyst such as $PtSn/Al_2O_3$, at a reaction temperature of 550° C., but this technology has the problem of short lifetime as well.

SUMMARY

Heterogeneous catalytic olefins preparation is normally conducted at very high temperatures in the range of 500-1,000° C. At these temperatures the chemical reactors themselves are behaving as a black body, emitting thermal radiation in the infrared spectral range, 1000-10,000 nm, with an output power P defined by the famous temperature to the power four, Stefan-Boltzmann radiation law. The hotter the black body the shorter the wavelength of the emitted radiation the peak wavelength, is given by Wein's displacement law. Thus, the emitted thermal radiation and the corresponding thermal energy could power the catalytic reaction simultaneously, namely black body photocatalysis or thermal radiative catalysis.

Therefore, an objective of the present disclosure is to provide a method of preparing an unsaturated hydrocarbon by thermal radiative catalyzing of the conversion of saturated hydrocarbon, aiming at solving the problems of high-energy consumption, low selectivity, and short lifetime of device and catalyst in the existing unsaturated hydrocarbon preparation process.

In order to achieve the above objective, the present disclosure provides a method of preparing an unsaturated hydrocarbon by thermal radiative catalyzing of the conversion of saturated hydrocarbon, wherein a saturated hydrocarbon reaction gas is introduced into a reaction furnace, and the saturated hydrocarbon is catalyzed to convert under heating and illumination conditions, so as to prepare the unsaturated hydrocarbon.

Preferably, the illumination has a wavelength in a range of visible light to infrared light, and the illumination is generated by thermal radiation of the heating modules.

Preferably, the heat module/source consists of high-radiance material with an emissivity constant higher than 0.1.

Preferably, the reaction furnace is a tubular reactor, the saturated hydrocarbon reaction gas is introduced into a reaction tube of the reaction furnace, and the reaction tube is made of a transparent high-temperature resistant material or a high-radiance material; or the reaction furnace is a cavity reactor, the saturated hydrocarbon reaction gas is introduced into a reaction cavity of the reaction furnace, and the heat source directly heats and thermally radiates the reaction gas.

Preferably, reaction temperature is 300-1300° C., and further preferably, 300~750° C.

Preferably, the reaction tube is heated by a heating module, such as heating rod or heating wire.

Preferably, the reaction tube is heated by the heating wire, and the heating wire is wrapped around the reaction tube.

Preferably, the step of introducing the saturated hydrocarbon reaction gas into the reaction furnace further includes: adding a catalyst into the reaction furnace, wherein the catalyst can absorb a spectrum generated by the heating module, so as to increase the temperature of the catalyst, and improve the internal energy of the reaction system; and the catalyst includes any one or more of a gaseous catalyst, a solid catalyst, and a liquid catalyst.

Preferably, the catalyst includes a gaseous catalyst, and the gaseous catalyst is a gas phase molecule with strong spectral absorption.

Preferably, the gaseous catalyst includes any one or more of carbon dioxide, methane, and water vapor.

Preferably, a catalytic temperature of the heating is 300-1300° C., and further preferably, 300~750° C.

Preferably, a flow rate of the saturated hydrocarbon is 1-1000 mL/min, and a volume ratio of the saturated hydrocarbon to the gaseous catalyst is (1000:1)~(1:1000).

Preferably, the catalyst includes a solid catalyst, and the solid catalyst includes a semiconducting material or a semimetallic material.

Preferably, a catalytic temperature of the heating is 300-1300° C., and further preferably, 300~750° C.

Preferably, the catalyst further includes a gaseous catalyst, and the gaseous catalyst includes any one or more of carbon dioxide, methane, and water vapor.

Preferably, the solid catalyst is a Zn/P25 catalyst; and

Preferably, a method of preparing the Zn/P25 catalyst includes: dissolving zinc acetate in water, adding P25 into the solution, stirring, drying, and then calcining to obtain the Zn/P25 catalyst.

Preferably, a loading amount of zinc in the Zn/P25 catalyst ranges 0.1%-20%.

Compared with the prior art, the present disclosure includes the following beneficial effects.

In the method of preparing unsaturated hydrocarbons by thermal radiative catalyzing of saturated hydrocarbons provided in the present disclosure, the photocatalysis is combined with the conventional thermal catalysis to improve the catalytic performance, accelerate the reaction speed, increase the conversion rate, and improve the selectivity of the catalytic reaction.

In the catalytic process, as long as the reactants, catalysts or reaction intermediates have visible to IR spectral absorption capability, the method of the present disclosure can further improve the catalytic performance/selectivity/stability and other characteristics on the basis of the original catalytic performance.

The present disclosure mainly aims at improving the catalytic performance of preparing unsaturated hydrocarbons via the conversion of saturated hydrocarbons. The method has the characteristics of being easy to operate and high stability, and does not require excessive modification on the existing industrial equipment. The present disclosure is not only suitable for producing ethylene by ethane steam pyrolysis to dehydrogenize, but also suitable for producing propylene by propane oxidative dehydrogenation and other reactions.

With this method, the reaction can be carried out at a saturated hydrocarbon flow rate of 1~1000 mL/min at 300° C.~1300° C. (preferably, 300° C.~750° C.), the conversion rate can be improved by 10~120% on the basis of the existing thermo-catalytic reaction, and the selectivity of generating the unsaturated hydrocarbon can be maintained at 90% or more.

BRIEF DESCRIPTION OF DRAWINGS

In order to illustrate the technical solutions of the examples of the present disclosure more clearly, the accompanying drawings required to be used in the examples will be briefly introduced below, and it should be understood that the following accompanying drawings show only certain examples of the present disclosure, thus they should not be seen as limitation on the scope of the present disclosure.

DETAILED DESCRIPTION OF EMBODIMENTS

Figure 1:
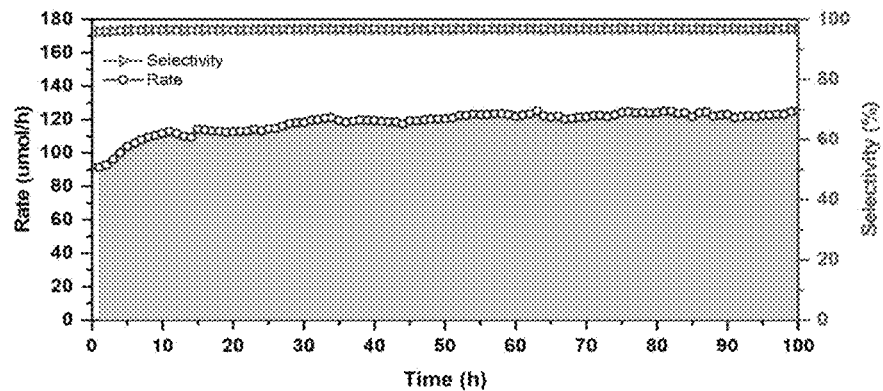
FIG. 1 is a graph of experimental results of stability and selectivity of preparing ethylene by homogeneous catalysis of ethane to dehydrogenize.

Regarding the terms used herein:

the term "black body photocatalysis" is synonymous with "thermal radiative catalysis" and indicate that the emitted thermal radiation and the corresponding thermal energy that power the catalytic reaction simultaneously.

the term "prepared from . . . " is synonymous with "comprising". The term "comprising", "including", "having", "containing" or any other derivatives thereof, as used herein, are intended to be non-exclusive. For example, a composition, step, method, article or apparatus comprising the listed elements is not necessarily only limited to those elements, but may include other elements not explicitly listed or elements inherent to such composition, step, method, article or apparatus.

The conjunction "consisting of . . . " excludes any unspecified element, step or component. If used in a claim, this phrase will make the claim be closed, so that the claim does not contain materials other than those described, but conventional impurities related thereto are excluded. When the phrase "consisting of . . . " appears in the clause of the claim rather than immediately after the subject matter, it only defines the elements described in the clause; and other elements are not excluded from said claim as a whole.

When the amount, concentration, or other values or parameters are expressed in a range, a preferred range, or a series of ranges defined by an upper preferred limit value and a lower preferred limit value, this should be understood as specifically disclosing all ranges formed by any pair of an upper value or a preferred value in any range and a lower value or a preferred value in any range, regardless of whether this range is separately disclosed. For example, when the range "1~5" is disclosed, the range described should be interpreted to include the ranges "1~4", "1~3", "1~2", "1~2 and 4~5", "1~3 and 5", etc. When a numerical range is described herein, unless otherwise specified, the range is intended to include its end values and all integers and fractions within this range.

In these examples, unless otherwise specified, all of the parts and percentages are counted by mass.

"Part by mass" denotes basic metering unit representing mass proportional relationships of a plurality of components, one part may denote any unit mass, for example, one part may represent 1 g, or may represent 2.689 g, etc. Assuming that the part by mass of a component A is a parts, and the part by mass of a component B is b parts, it means that the ratio of the mass of the component A to the mass of the component B is a:b. Alternatively, it means that the mass of the component A is aK, and the mass of the component B is bK (K is any number, and represents a multiplication factor). It should not be misunderstood that, unlike mass fraction, the sum of parts by mass of all components is not limited to 100 parts.

"And/or" is used to mean that one or both of the illustrated situations may occur, for example, A and/or B include (A and B) and (A or B).

The present disclosure provides a method of preparing unsaturated hydrocarbons by thermal radiative catalyzing of conversion of saturated hydrocarbons, wherein a saturated hydrocarbon reaction gas is introduced into a reaction furnace, and the saturated hydrocarbon is catalyzed to dehydrogenize under heating and illumination conditions to prepare the unsaturated hydrocarbons.

Specifically, the reaction furnace is a device for carrying out the catalytic reactions. The shape, structure and so on of the reaction furnace are not specifically limited, for example, the reaction furnace may be in a cubic shape, a cuboid shape, a cylindrical shape, or other irregular shapes. The reaction furnace may be, for example, a cavity reactor or a tubular reactor. The saturated hydrocarbon reaction gas may be alkanes such as ethane, propane or butane. If the reaction furnace is a cavity reactor, the reaction gas is introduced into a reaction cavity for catalytic reaction, and if the reaction furnace is a tubular reactor, the reaction gas is introduced into a reaction tube for catalytic reaction. Ethane is catalytically dehydrogenated to ethylene, propane is dehydrogenated to ethylene, propylene, and so on, and butane is dehydrogenated to obtain ethylene, propylene, butylene, and so on.

The preparation of the unsaturated hydrocarbon by saturated hydrocarbon dehydrogenization is mainly evaluated by two indexes, including conversion rate and selectivity, wherein the conversion rate is a ratio of an amount of products to an amount of raw materials used, and the higher the conversion rate is, the more the unsaturated hydrocarbons are obtained; and the selectivity refers to the probability of selecting to generate a desired product relative to byproducts during a certain reaction. As stated previously, there may be more than one unsaturated hydrocarbon prepared by saturated hydrocarbon dehydrogenization, therefore, in the process of the same catalytic reaction, the selectivity is different for different unsaturated hydrocarbons. The conversion rate and selectivity of the unsaturated hydrocarbon prepared by saturated hydrocarbon dehydrogenization in the solution of the present disclosure can be measured by an online gas chromatograph.

The existing preparation method of unsaturated hydrocarbons from saturated hydrocarbons mainly uses heating and a solid metal catalyst for catalytic reaction, and a reaction cavity or a reaction tube of the existing reaction furnace is generally made by using an ordinary opaque high-temperature resistant material. However, the applicant found that the heat source will conduct thermal radiation while providing heating, and the thermal radiation thereof can generate illumination, which also has a catalytic effect. The found thermal radiation catalysis is mainly divided into two parts, thermal radiation transfers thermal energy, and the thermal radiation spectrum can be used for driving photocatalysis, the vibration of a molecular bond of the saturated hydrocarbons is enhanced, and the internal energy of the reaction system is improved, so that the unsaturated hydrocarbons can be prepared from the saturated hydrocarbons.

It would readily occur to a person skilled in the art that although the solution of the present disclosure mainly uses the thermal radiation of the heat source to provide an illumination condition, the illumination can also be applied externally, as long as the catalytic condition for preparing an unsaturated hydrocarbon by the dehydrogenization of saturated hydrocarbon is satisfied. It should be noted that the term "illumination" in the present disclosure should be understood as a noun, rather than a verb, and cannot be understood as that the solution of the present disclosure must use a light source for illumination to limit the scope of protection of the solution of the present disclosure.

In the method of preparing an unsaturated hydrocarbon by thermal radiative catalyzing of the conversion of saturated hydrocarbon provided in the present disclosure, the photocatalysis is combined to the conventional thermal catalysis to improve the catalytic performance, accelerate the reaction speed, increase the conversion rate, and/or improve the selectivity of the catalytic reaction.

In a preferred solution, the illumination is generated by the thermal radiation in the heating process, so that the reaction furnace has a simple structure, and the existing industrial devices do not need to be excessively modified, an external illumination applying structure is not needed, and it only needs to prepare the heat source by a high-radiance material. Since the thermal radiation spectrum is mainly in the range of visible light to infrared light, the illumination wavelength in the photothermal catalysis of the solution of the present disclosure is preferably in the range of visible light to infrared light.

Preferably, a heat source for the heating includes a high-radiance material. For example, the heat source is a heating rod or a heating wire. The heating rod and the heating wire are of a common electrical heating structure, and are wrapped by a high-radiance material such as corundum and/or ceramic on an outer surface thereof. As the corundum and the ceramic themselves absorb a part of heat to increase the temperature, stronger thermal radiation than that of the heat source will be released. The heat source further may be prepared by coating the outer surface thereof with a black painted material with high radiance. It can be understood that, the high-radiance material included by the heat source is not limited to the illustrated cases, and other solutions of materials or structures are also within the scope of protection of the present disclosure as long as the high radiance is satisfied.

In an example, the reaction furnace is a tubular reactor, the saturated hydrocarbon reaction gas is introduced into a reaction tube of the reaction furnace, and the reaction tube is made of a transparent high-temperature resistant material or a high-radiance material, for example, a transparent quartz tube, an alumina-based corundum, a ceramic, etc.

It may be understood that, the reaction tube may be heated by an external heat source, or the reaction tube may be electrified to heat the reaction gas in the reaction tube. The reaction tube is made of a transparent high-temperature resistant material, so that the reaction tube can be penetrated by more thermal radiation of external heat source, to carry out thermal-radiation illumination on the reaction gas in the reaction tube. The reaction tube may also be made of a high-radiance material, so that after being heated, the reaction tube itself as a heat source can thermally radiate to illuminate the reaction gas inside the reaction tube.

It may be understood that the length of the distance between the heat source and the reaction gas is in inverse proportion to the magnitude of the thermal radiation spectrum generated during the process of the reaction gas being heated by the heat source; when the reaction tube is a transparent reaction tube, the radiance of the heat source is in direct proportion to the magnitude of the thermal radiation spectrum generated during the process of the reaction gas being heated by the heat source; when the reaction tube is made of a high-radiance material, the radiance of the reaction tube is in direct proportion to the magnitude of thermal radiation spectrum generated during the process of the reaction gas being heated by the heat source. Therefore, it may be understood that a person skilled in the art could adjust the conditions affecting the thermal radiation spectrum to a certain extent according to actual needs, as long as the catalytic temperature of heating of the heat source being 300~1300° C. is satisfied, for example, the catalytic temperature may be 300, 350, 400, 450, 500, 550, 600, 650, 700, 750, 800, 850, 900, 950, 1000, 1050, 1100, 1150, 1200, 1250 or 1300° C., or any value in 300~1300° C.

Optionally, a cavity structure further may be provided in the tubular reaction furnace, the reaction tube is installed in the cavity structure, and the heat source is also installed in the cavity structure, facilitating in releasing the thermal radiation.

In other examples, when the reaction furnace is a cavity reactor, the reaction gas is directly introduced into the reaction cavity for reaction, and the heat source directly heats and thermally radiates the reaction gas. Similar to the tubular reactor, the reaction cavity itself may also be electrified to heat as a heat source, or a heat source structure including a high-radiance material such as a heating rod or a heating wire is installed in the reaction cavity, so that thermal-radiation illumination is generated by the heating rod or the heating wire to act on the reaction gas.

In a preferred example, introducing the saturated hydrocarbon reaction gas into the reaction furnace further includes: adding a catalyst into the reaction furnace, wherein the catalyst can absorb a spectrum generated by the illumination, and improve the internal energy of the reaction system, so as to improve the catalytic performance; and the catalyst includes any one or more of a gaseous catalyst, a solid catalyst, and a liquid catalyst.

Specifically, adding the catalyst in the above photothermal catalysis reaction process can increase the catalytic rate. The characteristic of the catalyst is that it can absorb the spectrum generated by illumination, that is, it can absorb thermal radiation, so that the surface temperature of the catalyst itself is increased and the vibration is enhanced. The solid catalyst and the liquid catalyst further may excite the generation of photo-generated carriers or surface plasmas, and promote the activation of reactive gas molecules, thus accelerating the reaction rate. The method of the present disclosure can further improve the catalytic performance/selectivity/stability and other characteristics on the basis of the original catalytic performance.

The specific form of the catalyst is not limited, and the catalyst may be a gas (could be a substance with a gasification temperature lower than a catalytic temperature) capable of absorbing a spectrum, or a liquid (could be a substance with a melting temperature lower than a catalytic temperature) capable of absorbing a spectrum, and a solid catalyst.

In an example, the catalyst includes a gaseous catalyst. The gaseous catalyst is a gas molecule having strong spectrum absorption. The internal energy of the gaseous catalyst molecule itself is increased, which facilitates the transmission of kinetic energy during molecular collision. The gaseous catalyst includes any one or more of carbon dioxide, methane, and water vapor, and any other gas molecule capable of absorbing a spectrum.

More preferably, the gaseous catalyst is water vapor, wherein the water vapor has better spectral absorption characteristic, and thus better catalytic performance.

Preferably, when the gaseous catalyst is used, a catalytic temperature of the heating is 300~1300° C. The catalytic temperature may be, for example, 300, 350, 400, 450, 500, 520, 540, 550, 560, 580, 600, 620, 650, 680, 700, 750, 800, 850, 900, 950, 1000, 1050, 1100, 1150, 1200, 1250 or 1300° C., or any value in 300~1300° C. Preferably, the catalytic temperature is 300~750° C.; and more preferably, 400~750° C.

More preferably, a flow rate of introducing the saturated hydrocarbon into the reaction furnace is 1~1000 mL/min, for example, may be 1, 2, 3, 4, 4.4, 5, 6, 6.3, 7, 8, 9, 10, 20, 30, 50, 100, 200, 300, 400, 500, 600, 700, 800, 900 or 1000 mL/min, or any value in 1~1000 mL/min.

A volume ratio of the saturated hydrocarbon reaction gas to the gaseous catalyst is (1000:1)~(1:1000), for example, may be 2:1, 3:2, 5:3, 10:3, 50:3, 50:23, 100:33, 200:55, 300:57, 400:1, 500:1, etc.

In another example, the catalyst includes a solid catalyst, and the solid catalyst includes a semiconducting material, a semi-metallic material, an alloy or a metallic material. For example, the solid catalyst may be a semiconducting material such as titanium oxide, zinc oxide, and indium oxide, a semi-metallic material such as nickel phosphide, iron carbide, and titanium hydride, an alloy such as PdSn and PtZn or a metallic material such as Pt and Pd.

Preferably, when the solid catalyst is used, the catalytic temperature of the heating is 300~1300° C., for example, the catalytic temperature may be 300, 350, 400, 450, 500, 550, 600, 650, 700, 750, 800, 850, 900, 950, 1000, 1050, 1100, 1150, 1200, 1250 or 1300° C., or any value in 300~1300° C.

Preferably, the solid catalyst is a Zn/P25 catalyst. P25 is a commercial $TiO_2$ powder. Due to its strong photocatalytic activity, P25 is widely used as a photocatalyst in a series of photochemical reactions. Zn is loaded on P25 for doping modification to reduce a recombination rate of photo-generated electron-hole pairs, and improve the catalytic efficiency of the $TiO_2$ semiconducting material.

Preferably, a method of preparing the Zn/P25 catalyst is: dissolving zinc acetate in water, adding P25, stirring to react, drying, and then calcining to obtain the Zn/P25 catalyst.

Preferably, a loading amount of zinc in the Zn/P25 catalyst ranges 0.1%-20%.

Further, the catalyst may include a combination of a gaseous catalyst and a solid catalyst, for example, the above solid catalyst is used in combination with carbon dioxide or water vapor.

Optionally, the catalyst further may be a liquid catalyst, for example, a substance that is a liquid metal or liquid molten salt at a catalytic temperature. The catalyst further may be a combination of a liquid catalyst and a gaseous catalyst, and also may be a combination of a liquid catalyst and a solid catalyst.

Embodiments of the present disclosure will be described in detail below in combination with specific examples, while a person skilled in the art would understand that the following examples are merely for illustrating the present disclosure, but should not be considered as limitation on the scope of the present disclosure. If no specific conditions are specified in the examples, they are carried out under normal conditions or conditions recommended by manufacturers. If manufacturers of reagents or apparatuses used are not specified, they are conventional products commercially available.

Figure 5:
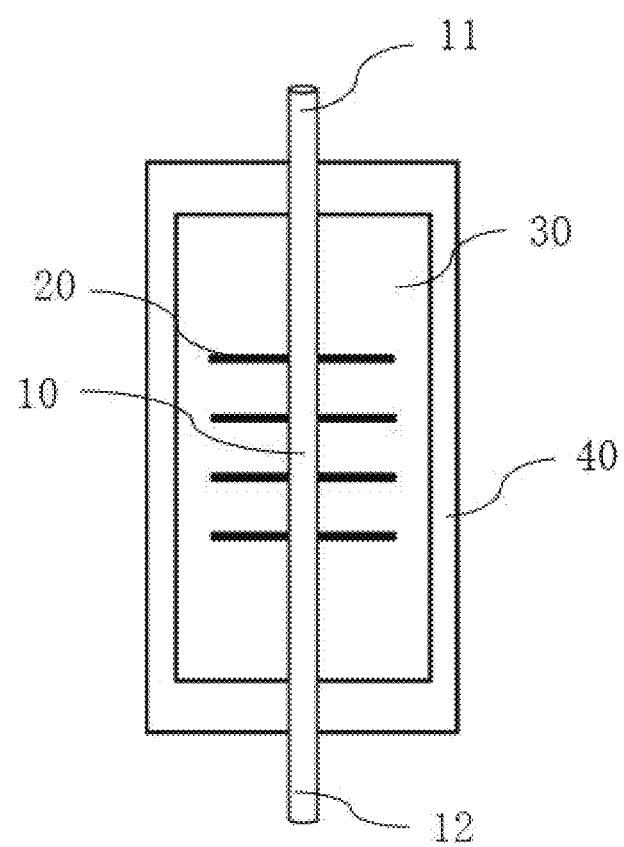
FIG. 5 is a structural schematic view of an example of a reaction furnace used in the method of the present disclosure.

For ease of description, a reaction furnace used in the method of preparing an unsaturated hydrocarbon by saturated hydrocarbon dehydrogenization in the examples of the present disclosure is described by taking a tubular reactor shown in FIG. 5 as an example. The reaction furnace includes a shell 40, and is provided with a cavity structure 30, and a reaction tube 10 and a heat source 20 are provided in the cavity structure 30, the reaction tube 10 includes a gas inlet 11 and a gas outlet 12 for introducing the reaction gas, a transparent quartz tube is adopted as the reaction tube 10, the heat source 20 is alumina-based electric heating rods with a high thermal radiance, a distance between the heating rods and the reaction tube 10 is about 5 cm, and the heating rods are uniformly installed around the reaction tube 10. A person skilled in the art could understand that the reaction furnace structure described herein is only used to describe the present disclosure, and should not be considered as limiting the scope of the present disclosure. Information such as specific structure and parameters of the reaction furnace can be modified or substituted according to practical applications. These modifications or substitutions do not make the corresponding technical solutions essentially depart from the scope of the technical solutions of various examples of the present disclosure.

Example 1

A method of preparing ethylene by dehydrogenization of ethane included the following specific steps:

mixing reaction gases according to a volume ratio of ethane 40% and Ar 60%, setting a temperature of a reaction furnace to 500° C., setting a flow rate of total reaction gas to 4.4 mL/min, and introducing the reaction gases into the reaction furnace. After one hour of reaction, it could be seen from results of external gas chromatography that an initial conversion rate of the reaction was about 0.047%, a production rate of ethylene was 2.02 μmol/h, and ethylene selectivity was 63.18%.

Example 2

It is different from Example 1 only in that the temperature of the reaction furnace was set to 520° C.

After one hour of reaction, it could be seen from results of external gas chromatography that an initial conversion rate of the reaction was about 0.079%, a production rate of ethylene was 4.12 μmol/h, and ethylene selectivity was 77.68%.

Example 3

It is different from Example 1 only in that the temperature of the reaction furnace was set to 540° C.

After one hour of reaction, it could be seen from results of external gas chromatography that an initial conversion rate of the reaction was about 0.19%, a production rate of ethylene was 11.86 μmol/h, and ethylene selectivity was 90.80%.

Example 4

It is different from Example 1 only in that the temperature of the reaction furnace was set to 560° C.

After one hour of reaction, it could be seen from results of external gas chromatography that an initial conversion rate of the reaction was about 0.41%, a production rate of ethylene was 26.13 μmol/h, and ethylene selectivity was 95.34%.

Example 5

It is different from Example 1 only in that the temperature of the reaction furnace was set to 580° C.

After one hour of reaction, it could be seen from results of external gas chromatography that an initial conversion rate of the reaction was about 1.21%, a production rate of ethylene was 50.53 μmol/h, and ethylene selectivity was 97.95%.

Example 6

It is different from Example 1 only in that the temperature of the reaction furnace was set to 600° C.

After one hour of reaction, it could be seen from results of external gas chromatography that an initial conversion rate of the reaction was about 1.81%, a production rate of ethylene was 82.75 μmol/h, and ethylene selectivity was 98.53%.

Example 1 to Example 6 are methods without a catalyst, i.e., ethylene is prepared by thermal radiative catalyzing of ethane to dehydrogenize only by heating and thermal radiation. The experimental results thereof are as shown in the column Without Catalyst in Table 1. According to Table 1, it can be seen that as the heating temperature is increased, both the conversion rate and selectivity of preparing ethylene by ethane dehydrogenization are gradually increased, moreover, when the heating temperature reaches 540° C., the selectivity reaches 90.8%, far higher than that in the prior art, and being comparable with the preparation method with a catalyst being added.

Example 7

A method of preparing ethylene by dehydrogenization of ethane included the following specific steps:

mixing reaction gases according to a volume ratio of ethane 40%, $CO_2$ 20%, and Ar 40%, setting a temperature of a reaction furnace to 500° C., setting a total reaction gas flow rate to 4.4 mL/min, and introducing the reaction gases into the reaction furnace for reaction. After one hour of reaction, it could be seen from results of external gas chromatography that an initial conversion rate of the reaction was about 0.09%, a production rate of ethylene was 5.56 μmol/h, and ethylene selectivity was 91.25%.

Example 8

It is different from Example 7 only in that the temperature of the reaction furnace was set to 520° C.

After one hour of reaction, it could be seen from results of external gas chromatography that an initial conversion rate of the reaction was about 0.24%, a production rate of ethylene was 15.37 μmol/h, and ethylene selectivity was 95.62%.

Example 9

It is different from Example 7 only in that the temperature of the reaction furnace was set to 540° C.

After one hour of reaction, it could be seen from results of external gas chromatography that an initial conversion rate of the reaction was about 0.64%, a production rate of ethylene was 42.09 μmol/h, and ethylene selectivity was 98.24%.

Example 10

It is different from Example 7 only in that the temperature of the reaction furnace was set to 560° C.

After one hour of reaction, it could be seen from results of external gas chromatography that an initial conversion rate of the reaction was about 1.2%, a production rate of ethylene was 79.71 μmol/h, and ethylene selectivity was 98.88%.

Example 11

It is different from Example 7 only in that the temperature of the reaction furnace was set to 580° C.

After one hour of reaction, it could be seen from results of external gas chromatography that an initial conversion rate of the reaction was about 2.2%, a production rate of ethylene was 147.24 μmol/h, and ethylene selectivity was 99.17%.

Example 12

It is different from Example 7 only in that the temperature of the reaction furnace was set to 600° C.

After one hour of reaction, it could be seen from results of external gas chromatography that an initial conversion rate of the reaction was about 3.6%, a production rate of ethylene was 242.65 μmol/h, and ethylene selectivity was 99.26%.

Example 7 to Example 12 are preparation methods with $CO_2$ as a catalyst, and experimental results thereof are as shown in the column $CO_2$ Catalyst in Table 1. According to Table 1, it can be seen that as the heating temperature is increased, the conversion rate and selectivity of preparing ethylene with ethane were gradually increased, moreover, after the addition of the $CO_2$ catalyst, even at 500° C., the selectivity can also reach 91.25%, indicating that the addition of the $CO_2$ catalyst improves the conversion rate and selectivity of preparing ethylene by thermal radiative catalyzing of ethane, rendering good conversion rate and selectivity at lower temperatures.

Example 13

A method of preparing ethylene by dehydrogenization of ethane included the following specific steps:

mixing reaction gases according to a volume ratio of ethane 50%, $H_2O$ vapor 5%, and Ar 45%, setting a temperature of a reaction furnace to 500° C., setting a total reaction gas flow rate to 4.4 mL/min, and introducing the reaction gases into the reaction furnace. After one hour of reaction, it could be seen from results of external gas chromatography that an initial conversion rate of the reaction was about 0.23%, a production rate of ethylene was 14.64 μmol/h, and ethylene selectivity was 95.56%.

Example 14

It is different from Example 13 only in that the temperature of the reaction furnace was set to 520° C.

After one hour of reaction, it could be seen from results of external gas chromatography that an initial conversion rate of the reaction was about 0.64%, a production rate of ethylene was 41.26 μmol/h, and ethylene selectivity was 95.97%.

Example 15

It is different from Example 13 only in that the temperature of the reaction furnace was set to 540° C.

After one hour of reaction, it could be seen from results of external gas chromatography that an initial conversion rate of the reaction was about 1.23%, a production rate of ethylene was 80.15 μmol/h, and ethylene selectivity was 97.38%.

Example 16

It is different from Example 13 only in that the temperature of the reaction furnace was set to 560° C.

After one hour of reaction, it could be seen from results of external gas chromatography that an initial conversion rate of the reaction was about 1.99%, a production rate of ethylene was 130.47 μmol/h, and ethylene selectivity was 97.67%.

Example 17

It is different from Example 13 only in that the temperature of the reaction furnace was set to 580° C.

After one hour of reaction, it could be seen from results of external gas chromatography that an initial conversion rate of the reaction was about 2.23%, a production rate of ethylene was 147.30 μmol/h, and ethylene selectivity was 98.34%.

Example 18

It is different from Example 13 only in that the temperature of the reaction furnace was set to 600° C.

After one hour of reaction, it could be seen from results of external gas chromatography that an initial conversion rate of the reaction was about 5.49%, a production rate of ethylene was 364.01 μmol/h, and ethylene selectivity was 98.87%.

Example 13 to Example 18 are methods for preparing ethylene by catalyzing ethane to dehydrogenize with water vapor, and experimental results thereof are as shown in the column $H_2O$ Vapor Catalyst in Table 1. According to Table 1, it can be seen that as the heating temperature is increased, the conversion rate and selectivity of preparing ethylene by catalyzing ethane to dehydrogenize with $H_2O$ vapor are gradually increased, and at 500° C., the conversion rate and selectivity of preparing ethylene by catalyzing ethane to dehydrogenize with $H_2O$ vapor are higher than those of $CO_2$, which may be due to the fact that the $H_2O$ vapor has better spectral absorption property than $CO_2$ at lower temperatures.

TABLE 1

Experimental Results of Preparing Ethylene by Ethane Dehydrogenization of Example 1 to Example 18

| | Without Catalyst | | | | $CO_2$ Catalyst | | | | $H_2O$ Vapor Catalyst | | |
|---|---|---|---|---|---|---|---|---|---|---|---|
| Examples | Temperature (° C.) | Conversion Rate | Selectivity | Examples | Temperature (° C.) | Conversion Rate | Selectivity | Examples | Temperature (° C.) | Conversion Rate | Selectivity |
| 1 | 500 | 0.047% | 63.18% | 7 | 500 | 0.09% | 91.25% | 13 | 500 | 0.23% | 95.56% |
| 2 | 520 | 0.079% | 77.68% | 8 | 520 | 0.24% | 95.62% | 14 | 520 | 0.64% | 95.97% |
| 3 | 540 | 0.19% | 90.80% | 9 | 540 | 0.64% | 98.24% | 15 | 540 | 1.23% | 97.38% |
| 4 | 560 | 0.41% | 95.34% | 10 | 560 | 1.2% | 98.88% | 16 | 560 | 1.99% | 97.67% |
| 5 | 580 | 1.21% | 97.95% | 11 | 580 | 2.2% | 99.17% | 17 | 580 | 2.23% | 98.34% |
| 6 | 600 | 1.81% | 98.53% | 12 | 600 | 3.6% | 99.26% | 18 | 600 | 5.49% | 98.87% |

TABLE 2

Production Rate of Preparing Ethylene by Ethane Dehydrogenization of Example 1 to Example 18

| | Without Catalyst | | | $CO_2$ Catalyst | | | $H_2O$ Vapor Catalyst | |
| --- | --- | --- | --- | --- | --- | --- | --- | --- |
| Examples | Temperature (° C.) | Production Rate (μmol/h) | Examples | Temperature (° C.) | Production Rate (μmol/h) | Examples | Temperature (° C.) | Production Rate (μmol/h) |
| 1 | 500 | 2.02 | 7 | 500 | 5.56 | 13 | 500 | 14.64 |
| 2 | 520 | 4.12 | 8 | 520 | 15.37 | 14 | 520 | 41.26 |
| 3 | 540 | 11.86 | 9 | 540 | 42.09 | 15 | 540 | 80.15 |
| 4 | 560 | 26.13 | 10 | 560 | 79.71 | 16 | 560 | 130.47 |
| 5 | 580 | 50.53 | 11 | 580 | 147.24 | 17 | 580 | 147.30 |
| 6 | 600 | 82.75 | 12 | 600 | 242.65 | 18 | 600 | 364.01 |

Table 2 shows statistical results of production rate of ethylene in preparing ethylene by ethane dehydrogenization of Example 1 to Example 18. According to Table 2, it can be seen that as the catalytic temperature is increased, the production rate of ethylene is increased, and at the same catalytic temperature, the production rate of ethylene is higher with the addition of the catalyst than without the catalyst.

The stability and selectivity of preparing ethylene by homogeneously catalyzing ethane to dehydrogenize are as shown in FIG. 1. FIG. 1 indicates that with the progress of the reaction, the selectivity of ethylene is gradually increased, and finally reaches 96% or above; and the production rate of ethylene is also increased gradually with the progress of the reaction, and finally is stabilized at 125 umol/h.

Figure 2:
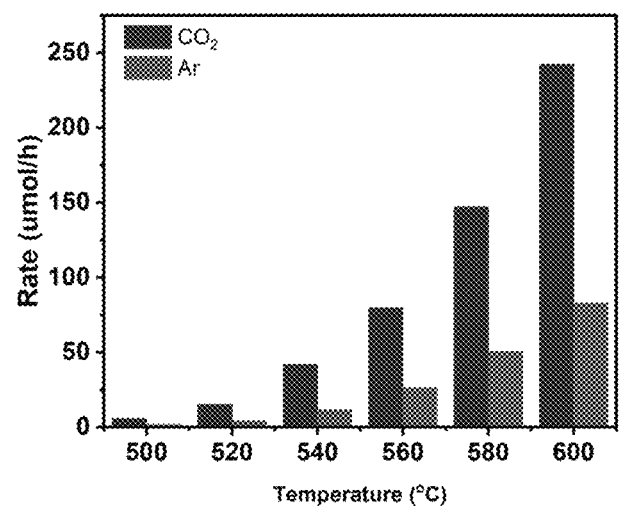
FIG. 2 is a comparison graph of ethylene rates of $CO_2$ and Ar systems.

The comparison result between the production rate of preparing ethylene by catalyzing ethane to dehydrogenize with the $CO_2$ and the production rate of ethylene without a catalyst and only with Ar as a protective gas is as shown in FIG. 2. FIG. 2 indicates that the production rate of ethylene of the $CO_2$ system is higher than that of the Ar system by 200% or more on average.

Example 19

A method of preparing an olefin by dehydrogenization of propane included the following specific steps:
mixing reaction gases according to a volume ratio of propane 50%, $H_2O$ vapor 3%, and Ar 47%, setting a temperature of a reaction furnace to 400° C., setting a total reaction gas flow rate to 6.3 mL/min, and introducing the reaction gases into the reaction furnace. After one hour of reaction, it could be seen from results of external gas chromatography that an initial conversion rate of the reaction was about 4.86%, ethylene selectivity was 36.82%, and propylene selectivity was 34.45%.

Example 20

It is different from Example 19 only in that the temperature of the reaction furnace was set to 450° C.
After one hour of reaction, it could be seen from results of external gas chromatography that an initial conversion rate of the reaction was about 5.16%, ethylene selectivity was 36.55%, and propylene selectivity was 46.72%.

Example 21

It is different from Example 19 only in that the temperature of the reaction furnace was set to 500° C.

After one hour of reaction, it could be seen from results of external gas chromatography that an initial conversion rate of the reaction was about 7.54%, ethylene selectivity was 35.47%, and propylene selectivity was 48.87%.

Example 22

It is different from Example 19 only in that the temperature of the reaction furnace was set to 550° C.

After one hour of reaction, it could be seen from results of external gas chromatography that an initial conversion rate of the reaction was about 13.04%, ethylene selectivity was 35.25%, and propylene selectivity was 49.16%.

Example 23

It is different from Example 19 only in that the temperature of the reaction furnace was set to 600° C.

After one hour of reaction, it could be seen from results of external gas chromatography that an initial conversion rate of the reaction was about 30.30%, ethylene selectivity was 37.54%, and propylene selectivity was 45.43%.

Example 24

It is different from Example 19 only in that the temperature of the reaction furnace was set to 650° C.

After one hour of reaction, it could be seen from results of external gas chromatography that an initial conversion rate of the reaction was 65.26%, ethylene selectivity was 43.78%, and propylene selectivity was 35.45%.

The experimental results of preparing an olefin by propane dehydrogenization of Example 19 to Example 24 are as shown in Table 3. According to Table 3, it can be seen that as the heating temperature is increased, the conversion rate of preparing ethylene and propylene by catalyzing propane to dehydrogenize with $H_2O$ vapor is gradually increased, indicating that more and more ethylene and propylene are produced, and as the heating temperature is increased, the selectivity of ethylene is gradually increased, and the selectivity of propylene is gradually decreased, gradually tending to be balanced. In practical applications, different reaction conditions can be selected according to different requirements to ethylene and propylene, and the amount of ethylene and propylene produced is adjusted.

TABLE 3

Experimental Results of Preparing Olefin by Propane
Dehydrogenization of Example 19 to Example 24
H$_2$O Vapor Catalyst

| Examples | Temperature (° C.) | Conversion rate | Selectivity Ethylene | Propylene |
|---|---|---|---|---|
| 19 | 400 | 4.86% | 36.82% | 34.45% |
| 20 | 450 | 5.16% | 36.55% | 46.72% |
| 21 | 500 | 7.54% | 35.47% | 48.87% |
| 22 | 550 | 13.04% | 35.25% | 49.16% |
| 23 | 600 | 30.30% | 37.54% | 45.43% |
| 24 | 650 | 65.26% | 43.78% | 35.45% |

Figure 3:
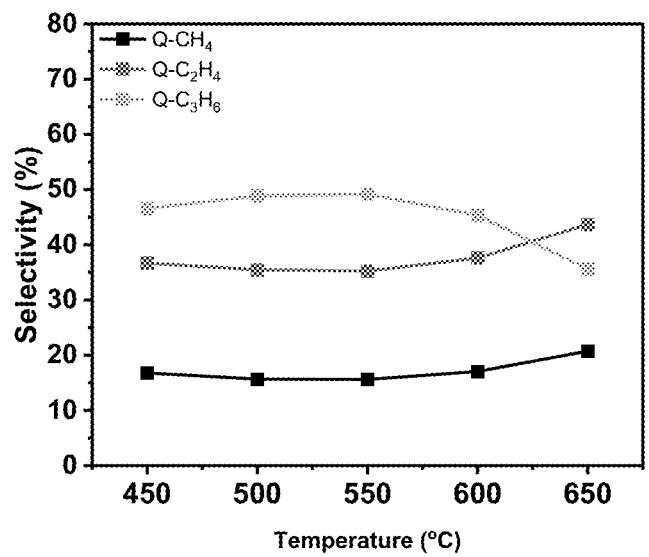
FIG. 3 is a graph of experimental results of selectivity of preparing an unsaturated hydrocarbon by dehydrogenization of propane of Example 19 to Example 24.

The selectivity of preparing an olefin by propane dehydrogenization of Example 19 to Example 24 is as shown in FIG. 3. FIG. 3 indicates that as the reaction temperature is increased, the selectivity for ethylene in low-carbon olefin is increased significantly.

Example 25

A method of preparing an olefin by dehydrogenization of butane included the following specific steps:
mixing reaction gases according to a volume ratio of butane 40%, CO$_2$ 20%, and Ar 40%, setting a temperature of a reaction furnace to 400° C., setting a total reaction gas flow rate to 4.4 mL/min, and introducing the reaction gases into the reaction furnace. After one hour of reaction, it could be seen from results of external gas chromatography that an initial conversion rate of the reaction was about 0.86%, ethylene selectivity was 0.87%, propylene selectivity was 0.81%, and butylene selectivity was 88.02%.

Example 26

It is different from Example 25 only in that the temperature of the reaction furnace was set to 450° C.
After one hour of reaction, it could be seen from results of external gas chromatography that an initial conversion rate of the reaction was about 1.52%, ethylene selectivity was 12.48%, propylene selectivity was 16.69%, and butylene selectivity was 52.14%.

Example 27

It is different from Example 25 only in that the temperature of the reaction furnace was set to 500° C.
After one hour of reaction, it could be seen from results of external gas chromatography that an initial conversion rate of the reaction was about 2.81%, ethylene selectivity was 19.64%, propylene selectivity was 25.74%, and butylene selectivity was 28.05%.

Example 28

It is different from Example 25 only in that the temperature of the reaction furnace was set to 550° C.
After one hour of reaction, it could be seen from results of external gas chromatography that an initial conversion rate of the reaction was about 4.89%, ethylene selectivity was 25.42%, propylene selectivity was 30.20%, and butylene selectivity was 16.13%.

The experimental results of preparing an olefin by butane dehydrogenization of Example 25 to Example 28 are as shown in Table 4. According to Table 4, it can be seen that as the heating temperature is increased, the conversion rate of preparing ethylene, propylene, and butylene by butane dehydrogenization is gradually increased, the selectivity of ethylene and propylene is also gradually increased, the selectivity of butylene is gradually reduced, and the selectivity of the three tends to be balanced. In practical applications, different reaction conditions can be selected according to different requirements to ethylene, propylene, and butylene, such that the amount of ethylene, propylene, and butylene produced is adjusted.

TABLE 4

Experimental Results of Preparing Olefin by Butane
Dehydrogenization of Example 25 to Example 28
CO$_2$ Catalyst

| Examples | Temperature (° C.) | Conversion Rate | Selectivity Ethylene | Propylene | Butylene |
|---|---|---|---|---|---|
| 25 | 400 | 0.86% | 0.87% | 0.81% | 88.02% |
| 26 | 450 | 1.52% | 12.48% | 16.69% | 52.14% |
| 27 | 500 | 2.81% | 19.64% | 25.74% | 28.05% |
| 28 | 550 | 4.89% | 25.42% | 30.20% | 16.13% |

Figure 4:
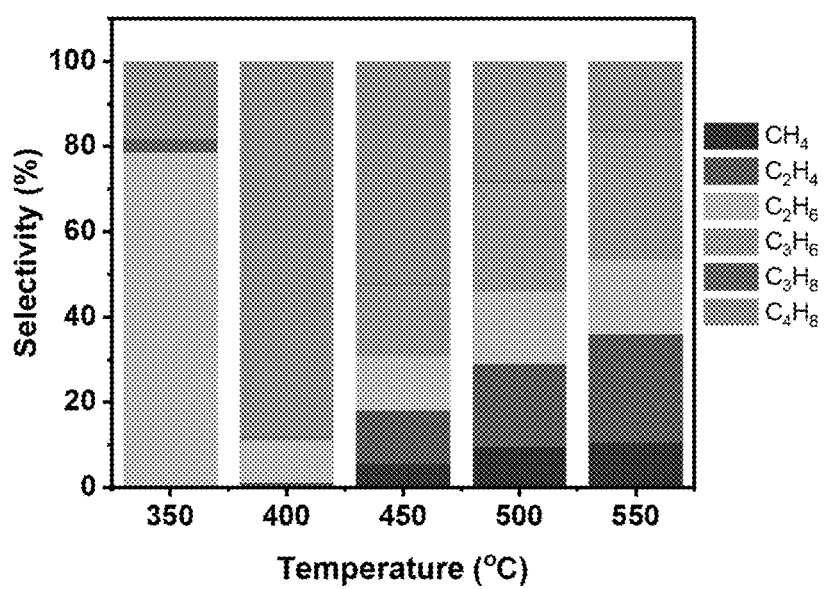
FIG. 4 is a graph of experimental results of selectivity of preparing an unsaturated hydrocarbon by dehydrogenization of butane of Example 25 to Example 28.

The selectivity of preparing an olefin by butane dehydrogenization of Example 25 to Example 28 is as shown in FIG. 4. FIG. 4 indicates that as the reaction temperature is increased, the selectivity for ethylene and propylene in low-carbon olefin is increased significantly.

Example 29

A solid catalyst was prepared by impregnation method with a commercial TiO$_2$-P25 as a carrier and metal Zn as an active component, with the following specific preparation steps:
dissolving 1.6 mg-320 mg of zinc acetate dihydrate in 4 mL of water, then adding 500 mg of P25, stirring for 24 h, drying at 60° C., then calcining at 600° C., and after grinding, obtaining a solid catalyst Zn/P25 with a loading amount of metal zinc ranging 0.1%-20 wt %.
In the above, for Zn/P25 with a loading amount of zinc being 1%, an input amount of zinc acetate dihydrate is 16 mg; for Zn/P25 with a loading amount of zinc being 2%, the input amount of zinc acetate dihydrate is 32 mg; and for Zn/P25 with a loading amount of zinc being 4%, the input amount of zinc acetate dihydrate is 64 mg.

Example 30

100 mg of Zn/P25 catalyst with a loading amount of zinc being 1% was loaded into a reaction tube. After reaction gases were mixed according to a volume ratio of ethane: Ar=1:2, a temperature of a reaction furnace was set to 550° C., a total reaction gas flow rate was set to 7.5 mL/min, and the reaction gases were introduced into the reaction furnace. After one hour of reaction, it could be seen from results of external gas chromatography that an initial conversion rate of the reaction was about 0.34%, and ethylene selectivity was 93.53%.

Example 31

It is different from Example 30 only in that the temperature of the reaction furnace was set to 575° C.

After one hour of reaction, it could be seen from results of external gas chromatography that an initial conversion rate of the reaction was about 0.69%, and ethylene selectivity was 96.14%.

Example 32

A method of preparing ethylene by ethane dehydrogenization included the following specific steps:
loading 100 mg of 4% Zn/P25 catalyst into a reactor, after mixing reaction gases according to a volume ratio of ethane: Ar=1:2, setting a reaction temperature to 600° C., setting a total reaction gas flow rate to 7.5 mL/min, and introducing the reaction gases into the reaction furnace. After one hour of reaction, it could be seen from results of external gas chromatography that an initial conversion rate of the reaction was about 2.04%, and ethylene selectivity was 93.45%.

Example 33

A method of preparing ethylene by ethane dehydrogenization included the following specific steps:
loading 100 mg of 4% Zn/P25 catalyst into a reactor, after mixing reaction gases according to a volume ratio of ethane: Ar=1:2, setting a reaction temperature to 625° C., setting a total reaction gas flow rate to 7.5 mL/min, and introducing the reaction gases into the reaction furnace. After one hour of reaction, it could be seen from results of external gas chromatography that an initial conversion rate of the reaction was about 5.84%, and ethylene selectivity was 95.87%.

Example 30 to Example 33 are methods of preparing ethylene by catalyzing ethane to dehydrogenize with a solid catalyst. Experimental results thereof are as shown in the column Solid Catalyst in Table 5. According to Table 5, it can be seen that the method of preparing an unsaturated hydrocarbon by thermal radiative catalyzing of saturated hydrocarbon of the present disclosure also may be realized with a solid catalyst, and can improve the conversion rate and selectivity compared with the method without a catalyst.

Example 34

100 mg of Zn/P25 catalyst with a loading amount of zinc being 1% was loaded into a reaction tube. After reaction gases were mixed according to a volume ratio of ethane: $CO_2$: Ar=1:1:1, a temperature of a reaction furnace was set to 550° C., a total reaction gas flow rate was set to 5.5 mL/min, and the reaction gases were introduced into the reaction furnace. After one hour of reaction, it could be seen from results of external gas chromatography that an initial conversion rate of the reaction was about 0.35%, and ethylene selectivity was 91.53%. Under the same conditions, when a stainless steel tube was sleeved outside a transparent quartz tube to reduce thermal radiation of a heating rod, the initial conversion rate of the reaction was 0.12%.

Example 35

It is different from Example 34 only in that the temperature of the reaction furnace was set to 575° C., and the flow rate of the total reaction gas was set to 7.5 mL/min.

After one hour of reaction, it could be seen from results of external gas chromatography that an initial conversion rate of the reaction was about 0.82%, and ethylene selectivity was 95.37%. Under the same conditions, when a stainless steel tube was sleeved outside a transparent quartz tube, the initial conversion rate of the reaction was 0.53%.

Example 36

It is different from Example 35 only in that the loading amount of zinc of Zn/P25 catalyst was 2%, and the temperature of the reaction furnace was set to 600° C.

After one hour of reaction, it could be seen from results of external gas chromatography that an initial conversion rate of the reaction was about 2.26%, and ethylene selectivity was 97.69%. Under the same conditions, when a stainless steel tube was sleeved outside a transparent quartz tube, the initial conversion rate of the reaction was 1.67%.

Example 37

It is different from Example 36 only in that the temperature of the reaction furnace was set to 625° C.

After one hour of reaction, it could be seen from results of external gas chromatography that an initial conversion rate of the reaction was about 6.01%, and ethylene selectivity was 98.48%. Under the same conditions, when a stainless steel tube was sleeved outside a transparent quartz tube, the initial conversion rate of the reaction was 4.85%.

Example 38

It is different from Example 36 only in that the temperature of the reaction furnace was set to 650° C.

After one hour of reaction, it could be seen from results of external gas chromatography that an initial conversion rate of the reaction was about 14.35%, and ethylene selectivity was 98.51%. Under the same conditions, when a stainless steel tube was sleeved outside a transparent quartz tube, the initial conversion rate of the reaction was 12.67%.

Example 34 to Example 38 use a solid catalyst and a $CO_2$ catalyst in combination to catalyze ethane to dehydrogenize to prepare ethylene, and experimental results thereof are as shown in Table 5. According to Table 5, it can be seen that for the preparation of ethylene by catalyzing ethane to dehydrogenize with the solid catalyst and the $CO_2$ catalyst, as the heating temperature is increased, both the conversion rate and selectivity of ethylene are gradually increased, and with respect to the photothermal catalysis method without adding a catalyst, the conversion rate and selectivity are still good at lower heating temperatures, indicating that the solid catalyst and the $CO_2$ catalyst can be used simultaneously.

TABLE 5

Experimental Results of Preparing Ethylene by Ethane Dehydrogenization of Example 30 to Example 38

| | Solid Catalyst | | | | | Solid Catalyst + CO$_2$ Catalyst | | | |
|---|---|---|---|---|---|---|---|---|---|
| Examples | Catalyst Content | Temperature (° C.) | Conversion Rate | Selectivity | Examples | Catalyst Content | Temperature (° C.) | Conversion Rate | Selectivity |
| 30 | 1% | 550 | 0.34% | 93.53% | 34 | 1% | 550 | 0.35% | 91.53% |
| 31 | 1% | 575 | 0.69% | 96.14% | 35 | 1% | 575 | 0.82% | 95.37% |
| 32 | 4% | 600 | 2.04% | 93.45% | 36 | 2% | 600 | 2.26% | 97.69% |
| 33 | 4% | 625 | 5.84% | 95.87% | 37 | 2% | 625 | 6.01% | 98.48% |
| | | | | | 38 | 2% | 650 | 14.35% | 98.51% |

Finally, it should be indicated that the various examples above are merely used for illustrating the technical solutions of the present disclosure, rather than limiting the present disclosure. While the detailed description is made to the present disclosure with reference to the various preceding examples, those ordinarily skilled in the art should understand that they still could modify the technical solutions recited in the various preceding examples, or make equivalent substitutions to some or all of the technical features therein. These modifications or substitutions do not make the essence of the corresponding technical solutions depart from the scope of the technical solutions of the various examples of the present disclosure.

Besides, a person skilled in the art could understand that although some examples described herein include certain features included in other examples rather than other features, combinations of features in different examples mean that they fall within the scope of the present disclosure and form different examples. For example, in the following claims, any of the examples claimed can be used in any combination manner. Information disclosed in the part of Background Art merely aims at deepening understanding to the overall background art of the present disclosure, but should not be regarded as acknowledging or implying in any form that the information constitutes prior art generally known by a person skilled in the art.

What is claimed is:

1. A method for preparing an unsaturated hydrocarbon by thermal radiative catalyzing of conversion of a saturated hydrocarbon, wherein a saturated hydrocarbon reaction gas is introduced into a reaction furnace, and under heating and illumination conditions, the saturated hydrocarbon is catalyzed to be dehydrogenized, so as to prepare the unsaturated hydrocarbon,
wherein introducing the saturated hydrocarbon reaction gas into the reaction furnace further comprises: adding a catalyst into the reaction furnace, the catalyst can absorb a spectrum generated by the illumination, so as to improve an internal energy of a reaction system, the catalyst comprises any one or more of a gaseous catalyst and a solid catalyst, the gaseous catalyst is a gas molecule having strong spectral absorption; and the solid catalyst is a Zn/P25 catalyst.

2. The method for preparing an unsaturated hydrocarbon by thermal radiative catalyzing of conversion of a saturated hydrocarbon according to claim 1, wherein the illumination has a wavelength in a range of UV to infrared light, and the illumination is generated by thermal radiation of a heating process.

3. The method for preparing an unsaturated hydrocarbon by thermal radiative catalyzing of conversion of a saturated hydrocarbon according to claim 2, wherein the reaction furnace is a tubular reactor, the saturated hydrocarbon reaction gas is introduced into a reaction tube of the reaction furnace, and the reaction tube is made of a transparent high-temperature resistant material or a high-radiance material; or the reaction furnace is a cavity reactor, the saturated hydrocarbon reaction gas is introduced into a reaction cavity of the reaction furnace, and the heat source directly heats and thermally radiates the reaction gas.

4. The method for preparing an unsaturated hydrocarbon by thermal radiative catalyzing of conversion of a saturated hydrocarbon according to claim 3, wherein a catalytic temperature of the heating is 300~1300° C.

5. The method for preparing an unsaturated hydrocarbon by thermal radiative catalyzing of conversion of a saturated hydrocarbon according to claim 2, wherein a catalytic temperature of the heating is 300~1300° C.

6. The method for preparing an unsaturated hydrocarbon by thermal radiative catalyzing of conversion of a saturated hydrocarbon according to claim 2, wherein, a heat source of the heating comprises a high-radiance material.

7. The method for preparing an unsaturated hydrocarbon by thermal radiative catalyzing of conversion of a saturated hydrocarbon according to claim 1, wherein a catalytic temperature of the heating is 300~4300° C.

8. The method for preparing an unsaturated hydrocarbon by thermal radiative catalyzing of conversion of a saturated hydrocarbon according to claim 1, wherein the gaseous catalyst comprises any one or more of carbon dioxide, methane, and water vapor.

9. The method for preparing an unsaturated hydrocarbon by thermal radiative catalyzing of conversion of a saturated hydrocarbon according to claim 8, wherein a flow rate of the saturated hydrocarbon is 1-1000 mL/min, and a volume ratio of the saturated hydrocarbon to the gaseous catalyst is (1000:1)~(1:1000).

10. The method for preparing an unsaturated hydrocarbon by thermal radiative catalyzing of conversion of a saturated hydrocarbon according to claim 8, wherein, a catalytic temperature of the heating is 300~1300° C.

11. The method for preparing an unsaturated hydrocarbon by thermal radiative catalyzing of conversion of a saturated hydrocarbon according to claim 1, wherein a method for preparing the Zn/P25 catalyst comprises: dissolving zinc acetate in water, adding P25 thereto, stirring to react, drying, and then calcining to obtain the Zn/P25 catalyst.

12. The method for preparing an unsaturated hydrocarbon by thermal radiative catalyzing of conversion of a saturated hydrocarbon according to claim 11, wherein a loading amount of zinc in the Zn/P25 catalyst ranges 0.1%-20%.

* * * * *